(12) United States Patent
DeCarlo

(10) Patent No.: US 8,181,995 B2
(45) Date of Patent: May 22, 2012

(54) COOL TIP JUNCTION

(75) Inventor: Arnold V. DeCarlo, Frederick, CO (US)

(73) Assignee: TYCO Healthcare Group LP, Mansfield, MA (US)

( * ) Notice: Subject to any disclaimer, the term of this patent is extended or adjusted under 35 U.S.C. 154(b) by 1292 days.

(21) Appl. No.: 11/899,921

(22) Filed: Sep. 7, 2007

(65) Prior Publication Data

US 2009/0069793 A1    Mar. 12, 2009

(51) Int. Cl.
*F16L 39/00* (2006.01)
*H02G 3/18* (2006.01)
*A61B 18/14* (2006.01)

(52) U.S. Cl. .......... 285/124.2; 174/650; 606/34; 606/41
(58) Field of Classification Search ............ 606/41, 606/34; 174/650; 285/124.2
See application file for complete search history.

(56) References Cited

U.S. PATENT DOCUMENTS

| | | | |
|---|---|---|---|
| 2,031,682 A | | 2/1936 | Frederick et al. |
| 3,183,302 A | * | 5/1965 | Wochner et al. ............ 174/138 F |
| 3,711,632 A | * | 1/1973 | Ghirardi ........................ 174/135 |
| 4,074,718 A | | 2/1978 | Morrison, Jr. et al. |
| 4,375,220 A | | 3/1983 | Matvias |
| 4,411,266 A | | 10/1983 | Cosman |
| 4,565,200 A | | 1/1986 | Cosman |
| 4,576,177 A | | 3/1986 | Webster, Jr. |
| 4,608,977 A | | 9/1986 | Brown |
| 4,662,383 A | | 5/1987 | Sogawa et al. |
| 4,739,759 A | | 4/1988 | Rexworth et al. |
| 4,832,024 A | | 5/1989 | Boussignac et al. |
| 4,880,719 A | | 11/1989 | Murofushi et al. |
| 4,961,435 A | | 10/1990 | Kitagawa et al. |
| 4,966,597 A | | 10/1990 | Cosman |
| 4,993,430 A | | 2/1991 | Shimoyama et al. |
| 5,029,588 A | | 7/1991 | Yock et al. |
| 5,103,804 A | | 4/1992 | Abele et al. |
| 5,225,741 A | | 7/1993 | Auld et al. |
| 5,230,623 A | | 7/1993 | Guthrie et al. |
| 5,233,515 A | | 8/1993 | Cosman |
| 5,246,438 A | | 9/1993 | Langberg |
| 5,267,994 A | | 12/1993 | Gentelia et al. |

(Continued)

FOREIGN PATENT DOCUMENTS

DE    2407559    2/1974

(Continued)

OTHER PUBLICATIONS

Cosman ER, Cosman BJ: "Methods of Making Nervous System Lesions", in William RH, Rengachary SS (eds): Neurosurgery. New York: McGraw-Hill, vol. 111, pp. 2490-2498, 1984.

(Continued)

*Primary Examiner* — Lee Cohen

(57) ABSTRACT

A conduit junction for use with an electrosurgical system includes a body having a lumen defined therein and at least one positioning structure. The lumen is configured to receive to receive at least a portion of a tubular structure. The tubular structure includes at least one of a conductor and a conduit of an electrosurgical system. The positioning structure is disposed in mechanical cooperation with the lumen and is adapted to position at least one of the conductor and the conduit within the body of the conduit junction. The body of the conduit junction may include a first section and a second section pivotably connected to each other. The positioning structure may include at least one rib pocket.

7 Claims, 4 Drawing Sheets

U.S. PATENT DOCUMENTS

| | | | |
|---|---|---|---|
| 5,281,213 A | 1/1994 | Milder et al. | |
| 5,323,778 A | 6/1994 | Kandarpa et al. | |
| 5,330,470 A | 7/1994 | Hagen | |
| 5,330,518 A | 7/1994 | Nielson et al. | |
| 5,334,193 A | 8/1994 | Nardella | |
| 5,342,357 A | 8/1994 | Nardella | |
| 5,348,554 A | 9/1994 | Imran et al. | |
| 5,370,675 A | 12/1994 | Edwards et al. | |
| 5,383,876 A | 1/1995 | Nardella | |
| 5,383,917 A | 1/1995 | Desai et al. | |
| 5,385,148 A | 1/1995 | Lesh et al. | |
| 5,403,311 A | 4/1995 | Abele et al. | |
| 5,409,000 A | 4/1995 | Imran | |
| 5,409,006 A | 4/1995 | Buchholtz et al. | |
| 5,417,686 A | 5/1995 | Peterson et al. | |
| 5,433,739 A | 7/1995 | Sluijter et al. | |
| 5,437,662 A | 8/1995 | Nardella | |
| 5,458,597 A | 10/1995 | Edwards et al. | |
| 5,462,521 A | 10/1995 | Brucker et al. | |
| 5,472,441 A | 12/1995 | Edwards et al. | |
| 5,490,850 A | 2/1996 | Ellman et al. | |
| 5,500,012 A | 3/1996 | Brucker et al. | |
| 5,520,684 A | 5/1996 | Imran | |
| 5,531,695 A * | 7/1996 | Swisher | 604/111 |
| 5,536,267 A | 7/1996 | Edwards et al. | |
| 5,571,147 A | 11/1996 | Sluijter et al. | |
| 5,588,432 A | 12/1996 | Crowley | |
| 5,599,345 A | 2/1997 | Edwards et al. | |
| 5,643,197 A | 7/1997 | Brucker et al. | |
| 5,647,871 A | 7/1997 | Levine et al. | |
| 5,662,111 A | 9/1997 | Cosman | |
| 5,684,274 A * | 11/1997 | McLeod | 174/92 |
| 5,688,267 A | 11/1997 | Panescu et al. | |
| 5,735,847 A | 4/1998 | Gough et al. | |
| 5,775,338 A | 7/1998 | Hastings | |
| 5,792,146 A | 8/1998 | Cosman | |
| 5,848,967 A | 12/1998 | Cosman | |
| 5,849,011 A | 12/1998 | Jones et al. | |
| 5,868,740 A | 2/1999 | LeVeen et al. | |
| 5,921,982 A | 7/1999 | Lesh et al. | |
| 5,943,719 A | 8/1999 | Feldman et al. | |
| 5,951,546 A | 9/1999 | Lorentzen | |
| 6,001,093 A | 12/1999 | Swanson et al. | |
| 6,006,126 A | 12/1999 | Cosman | |
| 6,053,912 A | 4/2000 | Panescu et al. | |
| 6,059,780 A | 5/2000 | Gough et al. | |
| 6,061,551 A | 5/2000 | Sorrells et al. | |
| 6,074,389 A | 6/2000 | Levine et al. | |
| 6,080,149 A | 6/2000 | Huang et al. | |
| 6,106,524 A | 8/2000 | Eggers et al. | |
| 6,132,426 A | 10/2000 | Kroll | |
| 6,146,380 A | 11/2000 | Racz et al. | |
| 6,162,216 A | 12/2000 | Guziak et al. | |
| 6,203,541 B1 | 3/2001 | Keppel | |
| 6,241,725 B1 | 6/2001 | Cosman | |
| 6,246,912 B1 | 6/2001 | Sluijter et al. | |
| 6,287,305 B1 | 9/2001 | Heim et al. | |
| 6,306,132 B1 | 10/2001 | Moorman et al. | |
| 6,333,464 B1 * | 12/2001 | Ellison | 174/92 |
| 6,337,998 B1 | 1/2002 | Behl et al. | |
| 6,432,070 B1 | 8/2002 | Talish et al. | |
| 6,478,793 B1 | 11/2002 | Cosman et al. | |
| 6,500,172 B1 | 12/2002 | Panescu et al. | |
| 6,506,189 B1 | 1/2003 | Rittman, III et al. | |
| 6,530,922 B2 | 3/2003 | Cosman et al. | |
| 6,575,969 B1 | 6/2003 | Rittman, III et al. | |
| 6,605,085 B1 | 8/2003 | Edwards | |
| 6,613,047 B2 | 9/2003 | Edwards | |
| 6,685,729 B2 | 2/2004 | Gonzalez | |
| 6,918,907 B2 | 7/2005 | Kelly et al. | |
| 7,012,194 B1 * | 3/2006 | Wang | 174/92 |
| 7,137,980 B2 | 11/2006 | Buysse et al. | |
| 7,156,842 B2 | 1/2007 | Sartor et al. | |
| 7,179,255 B2 | 2/2007 | Lettice et al. | |
| 7,186,222 B1 | 3/2007 | Callister et al. | |
| 7,201,600 B2 * | 4/2007 | Sokol et al. | 439/367 |
| 7,207,989 B2 | 4/2007 | Pike, Jr. et al. | |
| 7,218,958 B2 | 5/2007 | Rashidi | |
| 7,235,070 B2 | 6/2007 | Vanney | |
| 7,235,073 B2 | 6/2007 | Levine et al. | |
| 7,238,184 B2 | 7/2007 | Megerman et al. | |
| 7,264,619 B2 | 9/2007 | Venturelli | |
| 7,278,991 B2 | 10/2007 | Morris et al. | |
| 7,282,049 B2 | 10/2007 | Orszulak et al. | |
| 7,294,127 B2 | 11/2007 | Leung et al. | |
| 7,294,143 B2 | 11/2007 | Francischelli | |
| 7,302,285 B2 | 11/2007 | Fuimaono et al. | |
| 7,303,558 B2 | 12/2007 | Swanson | |
| 7,331,947 B2 | 2/2008 | McGuckin, Jr. et al. | |
| RE40,156 E | 3/2008 | Sharps et al. | |
| 7,341,586 B2 | 3/2008 | Daniel et al. | |
| 7,344,533 B2 | 3/2008 | Pearson et al. | |
| 7,364,578 B2 | 4/2008 | Francischelli et al. | |
| 7,364,579 B2 | 4/2008 | Mulier et al. | |
| 7,367,974 B2 | 5/2008 | Haemmerich et al. | |
| 7,367,975 B2 | 5/2008 | Malecki et al. | |
| 7,387,625 B2 | 6/2008 | Hovda et al. | |
| 7,419,486 B2 | 9/2008 | Kampa | |
| 7,419,487 B2 | 9/2008 | Johnson et al. | |
| 7,419,488 B2 | 9/2008 | Ciarrocca et al. | |
| 7,419,489 B2 | 9/2008 | Vanney et al. | |
| 7,422,587 B2 | 9/2008 | Bek et al. | |
| 7,432,445 B2 * | 10/2008 | Bird et al. | 174/92 |
| 7,480,533 B2 | 1/2009 | Cosman et al. | |
| 2001/0034518 A1 | 10/2001 | Edwards et al. | |
| 2002/0058933 A1 | 5/2002 | Christopherson et al. | |
| 2002/0111615 A1 | 8/2002 | Cosman et al. | |
| 2002/0120261 A1 | 8/2002 | Morris et al. | |
| 2002/0156472 A1 | 10/2002 | Lee et al. | |
| 2003/0018247 A1 | 1/2003 | Gonzalez | |
| 2004/0002745 A1 | 1/2004 | Fleming et al. | |
| 2004/0039429 A1 | 2/2004 | Daniel et al. | |
| 2004/0181216 A1 | 9/2004 | Kelly et al. | |
| 2004/0199161 A1 | 10/2004 | Truckai et al. | |
| 2004/0254573 A1 | 12/2004 | Dycus | |
| 2004/0267256 A1 | 12/2004 | Garabedian et al. | |
| 2005/0096681 A1 | 5/2005 | Desinger et al. | |
| 2005/0107784 A1 | 5/2005 | Moses | |
| 2005/0107785 A1 | 5/2005 | Dycus | |
| 2005/0113824 A1 | 5/2005 | Sartor et al. | |
| 2005/0119655 A1 | 6/2005 | Moses | |
| 2005/0154387 A1 | 7/2005 | Moses | |
| 2005/0155743 A1 | 7/2005 | Getz, Jr. et al. | |
| 2005/0192564 A1 | 9/2005 | Cosman et al. | |
| 2006/0079885 A1 | 4/2006 | Rick et al. | |
| 2006/0079887 A1 | 4/2006 | Buysse | |
| 2007/0046260 A1 | 3/2007 | Ishikawa | |
| 2007/0066971 A1 | 3/2007 | Podhajsky | |
| 2007/0073285 A1 | 3/2007 | Peterson | |
| 2007/0078453 A1 | 4/2007 | Johnson | |
| 2007/0078454 A1 | 4/2007 | McPherson | |
| 2007/0258838 A1 | 11/2007 | Drake et al. | |
| 2007/0260240 A1 | 11/2007 | Rusin | |
| 2008/0021448 A1 | 1/2008 | Orszulak | |
| 2008/0027424 A1 | 1/2008 | DeCarlo et al. | |
| 2008/0183165 A1 | 7/2008 | Buysse et al. | |
| 2008/0287946 A1 | 11/2008 | DeCarlo et al. | |
| 2008/0319438 A1 | 12/2008 | DeCarlo | |

FOREIGN PATENT DOCUMENTS

| | | |
|---|---|---|
| DE | 10224154 | 12/2003 |
| EP | 0171967 A | 2/1986 |
| EP | 0246350 | 11/1987 |
| EP | 0310431 | 4/1989 |
| EP | 0608609 | 8/1994 |
| EP | 1070518 A2 | 1/2001 |
| EP | 1465037 A | 10/2004 |
| EP | 1645234 | 4/2006 |
| EP | 1656900 | 5/2006 |
| FR | 2862813 | 5/2005 |
| FR | 2864439 | 7/2005 |
| WO | WO 93/24066 | 12/1993 |
| WO | WO 94/28809 | 12/1994 |
| WO | WO 96/04860 | 2/1996 |
| WO | WO 96/18349 | 6/1996 |
| WO | WO 96/29946 | 10/1996 |
| WO | WO 96/34571 | 11/1996 |

| WO | WO 96/39914 | 12/1996 |
| WO | WO 97/06739 | 2/1997 |
| WO | WO 97/06740 | 2/1997 |
| WO | WO 97/06855 | 2/1997 |
| WO | WO 97/17029 | 5/1997 |
| WO | WO 99/01074 | 1/1999 |
| WO | WO 99/04710 | 2/1999 |
| WO | WO 99/22657 | 5/1999 |
| WO | WO 00/67846 | 11/2000 |
| WO | WO 01/00114 A1 | 1/2001 |
| WO | WO 2004/045436 | 6/2004 |
| WO | WO 2005/009528 | 2/2005 |
| WO | WO 2006/068430 | 6/2006 |

OTHER PUBLICATIONS

Anderson, Gary et al., "A numerical study of rapid heating for high temperature radio frequency hyperthermia", International Journal of Bio-Medical Computing, 35 (1994) 297-307.

Goldberg, et al., "Tissue Ablation with Radiofrequency: Effective Probe Size, Gauge, Duration and Temperature and Lesion Volume", Acad Radio, 1995, vol. 2, No. 5, pp. 399-404.

Melvin A. Astrahan, "A Localized Current Field Hyperthermia System for Use with 192-Iridium Interstitial Implants", Medical Physics, 9(3), May/Jun. 1982.

Cosman et al. "Theoretical Aspects of Radiofrequency Lesions in the Dorsal Root Entry Zone". Neurosurgery 15:945-950, 1984.

Stuart W. Young, Nuclear Magnetic Resonance Imaging—Basic Principles, Raven Press, New York, 1984.

E.R. Cosman, et al., "Radiofrequency Lesion Generation and its Effect on Tissue Impedence", Applied Neurophysiology, 51:230-242, 1988.

K. Ogata, Modern Control Engineering, Prentice-Hall, Englewood Cliffs, N.J., 1970.

E. Alexander et al., "Magnetic resonance image-directed stereotactic neurosurgery: use of image fusion with computerized tomography to enhance spatial accuracy", J. Neurosurg., 83:271, 276, 1995.

Reidenbach (1995) "First Experimental Results with Special Applicators for High-Frequency Interstitial Thermotherapy", Society Minimally Ivasive Therapy, 4(Supp1.1):40 (Abstr).

Organ LW. (1976) "Electrophysiologic Principles of Radiofrequency Lesion Making" Appl. Neurophysiol, vol. 39: pp. 69-76.

Livraghi et al. (1995) "Saline-enhanced RF Tissue Ablation in the Treatment of Liver Metastases", Radiology, 205-210.

Solbiati et al. (1995) "Percutaneous US-guided RF Tissue Ablation of Liver Metastases: Long-term Follow-up", Radiology, 197(P): 199.

Solbiati, et al. (2001) "Percutaneous Radio-frequency Ablation of Hepatic Metastases from Colorectal Cancer: Long-term Results in 117 Patients", *Radiology*, vol. 221, pp. 159-166.

Goldberg, et al., "Image-guided Radiofrequency Tumor Ablation: Challenges and Opportunities—Part I", (2001) *J Vasc. Interv. Radiol*, vol. 12, pp. 1021-1032.

McGahan et al. (1995) "Percutaneous Ultrasound-guided Radiofrequency Electrocautery Ablation of Prostate Tissue in Dogs", Acad Radiol, vol. 2, No. 1:pp. 61-65.

Goldberg et al. (1995) "Tissue Ablation with Radiofrequency Using Multiprobe Arrays", Acad Radiol, vol. 2: pp. 399-404.

Goldberg et al. (1995) "Saline-enhanced RF Ablation: Demonstration of Efficacy and Optimization of Parameter", Radiology, 197(P): 140 (Abstr).

Bulletin of the American Physical Society, vol. 47, No. 5, Aug. 2002.

European Search Report from Application EP 05021935 dated Jan. 27, 2006.

European Search Report from Application EP 05021939 dated Jan. 27, 2006.

European Search Report from Application EP 05021025 dated Mar. 13, 2006.

European Search Report from Application EP 05021936.9 dated Feb. 6, 2006.

European Search Report from Application EP 05025423.4 dated Jan. 12, 2007.

European Search Report from Application EP 06019768 dated Jan. 8, 2007.

European Search Report from Application EP 05025424 dated Jan. 23, 2007.

European Search Report from Application EP 07009028 dated Jul. 16, 2007.

McRury, Ian D., (2000) "The Effect of Ablation Sequence and Duration on Lesion Shape Using Rapidly Pulsed Radiofrequency Energy Through Electrodes", Springer Netherlands, vol. 4, No. 1, pp. 307-320.

* cited by examiner

COOL TIP JUNCTION

BACKGROUND

1. Technical Field

The present disclosure relates generally to methods and apparatuses for thermal treatment of tissue and, more particularly, to a conduit junction for use with an electrosurgical system configured to secure conduits in place in the electrosurgical system.

2. Background of the Related Art

Electrosurgical systems are well known in the art. Some electrosurgical systems employ microwave energy to produce a number of therapeutic effects in or on tissue at a target surgical site during any number of non-specific surgical procedures. Many electrosurgical systems transmit microwave energy as well as other kinds of energy through conductors, such as, wires, cables, tubing or other suitable energy transmission structure. In addition to the energy transmitting conductors, some electrosurgical systems have conduits adapted to carry cooling fluids to the surgical tip of the electrosurgical system. These conduits transport cooling fluid to the surgical tip of the electrosurgical system to transfer heat between the surgical tip and the fluid.

Ideally, the maximum amount of cooling fluid should reach the surgical tip and, therefore, the conduits should not have leaks. To this end, manufacturers of electrosurgical systems usually test these conduits for leakage. During quality inspection, if a leak is found in the conduits, the entire electrosurgical system is often discarded.

SUMMARY

The present disclosure relates to a conduit junction for use with an electrosurgical system. The conduit junction includes a body having a lumen defined therein and at least one positioning structure. The lumen of the body is configured to receive at least a portion of the tubular structure. The tubular structure includes at least one of a conductor and a conduit. The positioning structure is disposed in mechanical cooperation with the lumen and is adapted to position at least one of the conductor and the conduit within the body of the conduit junction.

The present disclosure also relates to an electrosurgical system. The electrosurgical system includes a surgical device, a tubular structure, and a conduit junction. The tubular structure includes a conduit defined therein and a conductor. The conduit is configured to carry fluid towards the surgical device. The conductor is configured to deliver energy to the surgical device. The conduit junction has at least one positioning structure adapted to position at least one of the conductor and the conduit.

The present disclosure additionally relates to a method of assembling an electrosurgical system. This method includes the steps of providing an electrosurgical system having a first and second sections, and a conduit junction including at least one positioning structure. Further, the method includes the step of connecting the first section and the second section of the electrosurgical system to the conduit junction.

BRIEF DESCRIPTION OF THE DRAWINGS

Embodiments of the presently disclosed electrosurgical system and conduit junction for use therewith are disclosed herein with reference to the drawings, wherein.

DETAILED DESCRIPTION OF THE EMBODIMENTS

Figure 1:
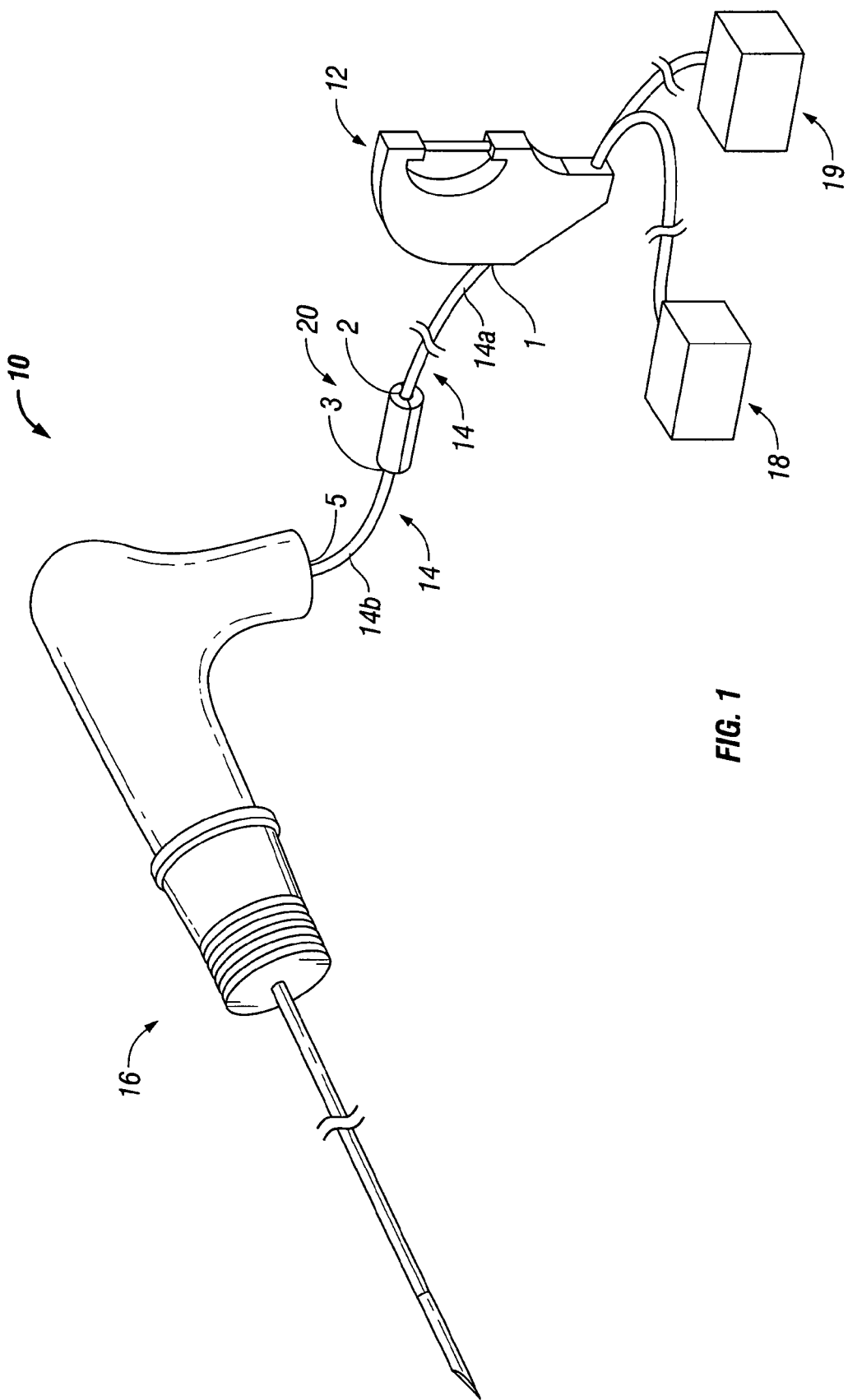
FIG. 1 is a perspective view of an electrosurgical system according to an embodiment of the present disclosure.

Embodiments of the presently disclosed electrosurgical system and conduit junction for use therewith are described in detail with reference to the drawings, in which like reference numerals designate identical or corresponding elements in each of the several views. As used herein and as is traditional, the term "distal" refers to the portion that is farther from the user and the term "proximal" refers to the portion that is closer the user. Also, in the specification and the claims, all singular forms, including "a," "an," and "the," include the plural reference unless the context clearly dictates otherwise. Likewise, all plural forms include the singular reference.

The conduit junction of the present disclosure is intended to be used with an electrosurgical system or any other suitable surgical system. Generally, electrosurgical systems deliver electrosurgical energy to tissue for thermal treatment such as tissue ablation, tissue vaporization and tissue coagulation. For example, radio frequency (RF) energy may be applied to tissue to treat benign prostatic hyperplasia (BPH). The applications of electrosurgical systems, however, are not limited to the treatment of BPH. Surgeons often employ electrosurgical systems in other kinds of surgical procedures such as cardiac ablation, cancer treatment, among others. Some electrosurgical systems are designed for use during minimally invasive procedures.

The present disclosure relates to a conduit junction that interconnects at least two portions of an electrosurgical system. Specifically, the presently disclosed conduit junction operatively couples conduits and conductors of an electrosurgical system. Since the conduit junction joins at least two portions of an electrosurgical system, the conduits and conductors do not need to extend throughout the entire length of the system. The conduits and conductors of the present disclosure can be shorter than the conduits and conductors of typical electrosurgical systems. The shorter length of these conduits allows manufacturers to perform leak testing more efficiently. Also, if a leak or any other manufacturing defect is detected in the electrosurgical system of the present disclosure, it is envisioned that only the flawed portion of the electrosurgical system may be replaced or repaired. The remaining portion of the electrosurgical system can be saved and reused.

Figure 2:
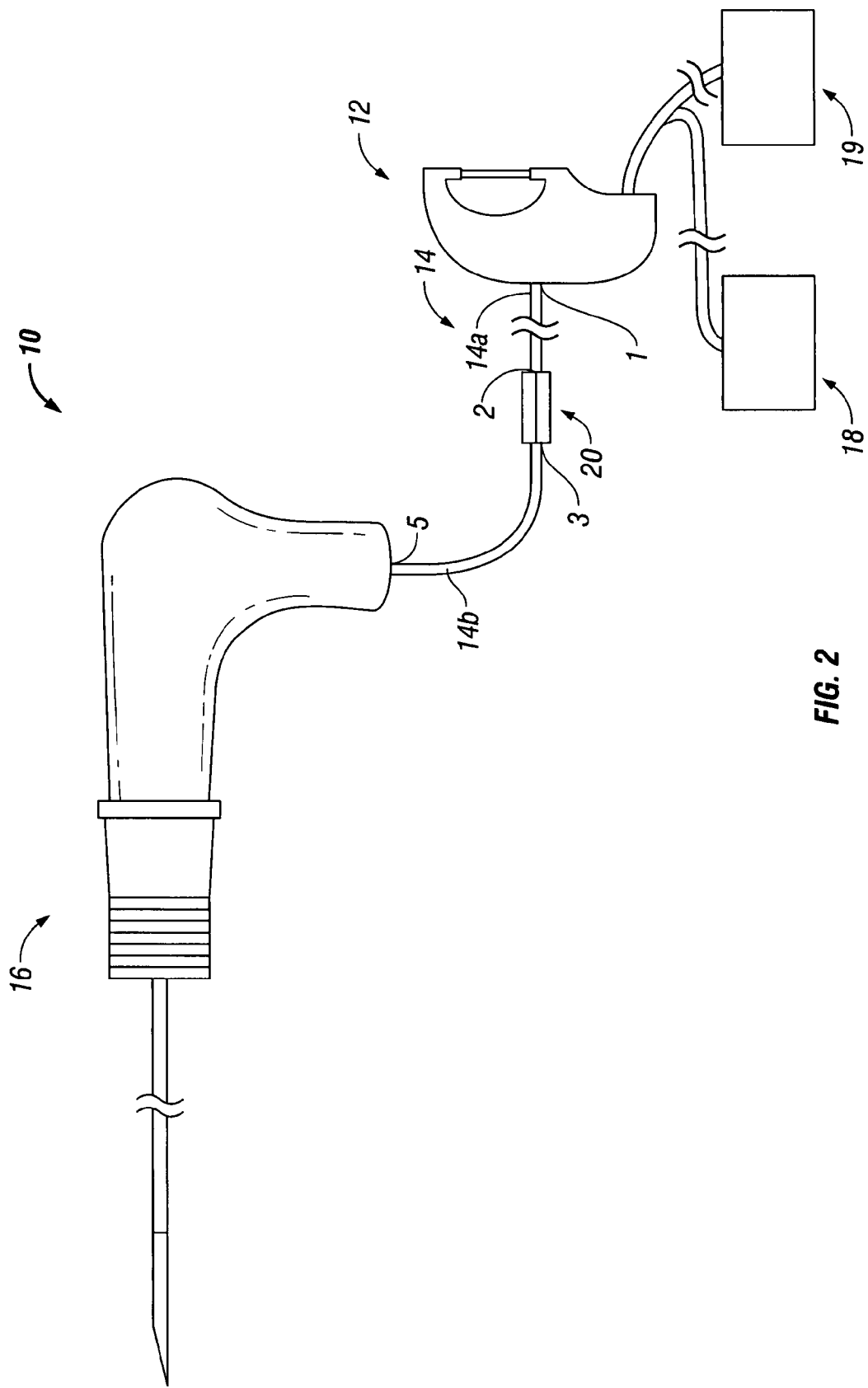
FIG. 2 is a side elevational view of the electrosurgical system of FIG. 1.

Referring initially to FIGS. 1 and 2, an electrosurgical system is generally designated as reference numeral 10. The present disclosure is not limited to any specific kind of electrosurgical system. Rather, electrosurgical system 10 can be a microwave ablation system, an RF system or any other suitable surgical system. In an embodiment, electrosurgical system 10 includes a handle assembly 12, a tubular structure 14, a conduit junction 20, and a surgical device 16. Handle assembly 12 is attached to the proximal end of tubular structure 14. In turn, the distal end of the tubular structure 14 is operatively fixed to surgical device 16. Surgical device 16 can be any suitable surgical apparatus, such as an ablation instrument, a microwave antenna, or an RF probe.

Figure 3:
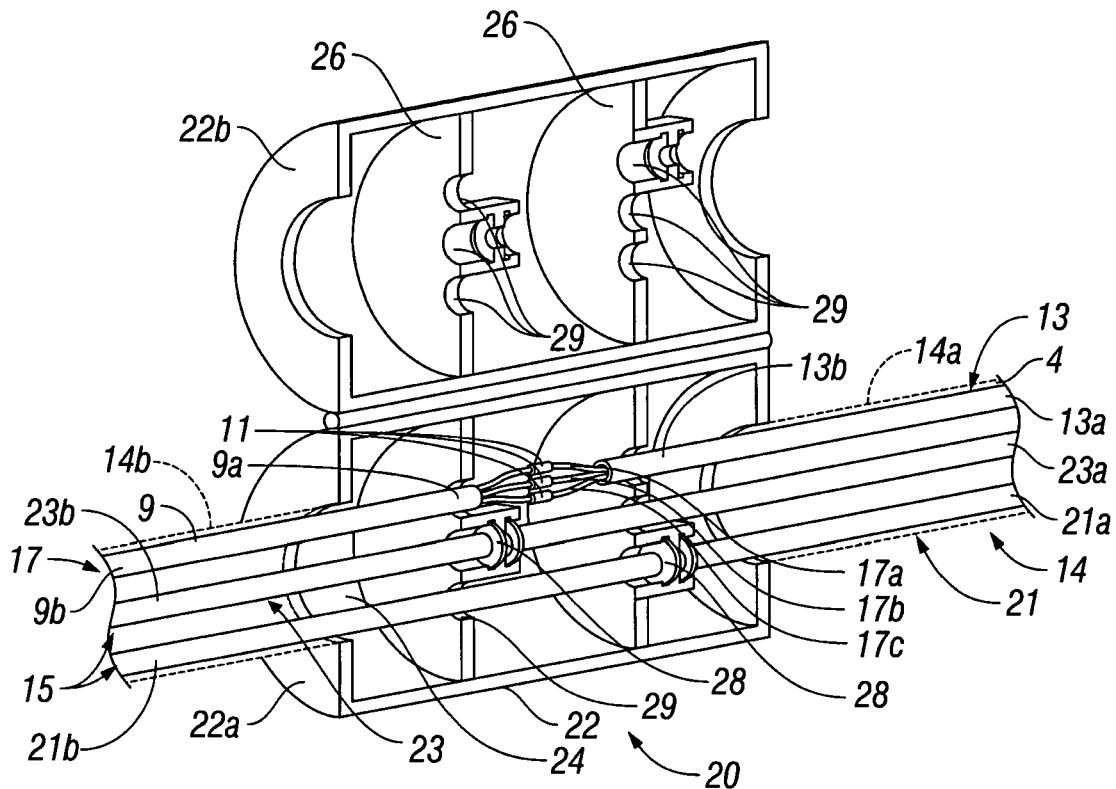
FIG. 3 is a perspective view a conduit junction according to an embodiment of the present disclosure in an open position.

Tubular structure 14 has a lumen or a bore 4 extending therethrough, as seen in FIG. 3. Bore 4 is adapted to receive at least one conductor 17 and a conduit 15. Tubular structure 14 can be made of an electrically and thermally insulative material. As shown in FIGS. 1 and 2, tubular structure 14 includes a first section 14a secured to the handle assembly 12 and a second section 14b fixed to surgical device 16. A conduit junction 20 interconnects first section 14a and second section 14b of tubular structure 14 with each other. In particular, a proximal end 1 of first section 14a is secured to handle assembly 12 and a distal end 2 of first section 14a is attached to conduit junction 20. A proximal end 3 of second section 14b, in turn, is connected to conduit junction 20 and a distal end 5 of second section 14b is secured to surgical device 16.

As seen in FIGS. 1 and 3, an electrosurgical generator 19 supplies energy to electrosurgical system 10 and is in electromechanical cooperation with conductor 17. The energy supplied by electrosurgical energy generator 19 is carried towards surgical device 16 through conductor 17. Accordingly, conductor 17 is capable of transmitting electrosurgical energy therethrough and may extend from handle assembly 12 to surgical device 16. The present disclosure envisions that conductor 17 can be made of any suitable electrically conductive material. Additionally, it is contemplated that conductor 17 can be formed of wires, cables, or any suitable energy transmitting apparatus. Conductor 17 can include one or more energy transmitting apparatuses. In the embodiment depicted in FIG. 3, for instance, conductor 17 includes three wires 17a, 17b, and 17c. It is also envisioned that conductor 17 includes a first section 13 and a second section 9 in electromechanical cooperation with each other.

With reference to FIGS. 3 and 6, conduit junction 20 operatively interconnects first section 13 and second section 9 of conductor 17. In particular, a proximal end 13a of first section 13 is connected to handle assembly 12 and a distal end 13b of first section 13 is positioned within to conduit junction 20. A proximal end 9a of second section 9 is positioned within conduit junction 20 and a distal end 9b of second section 9 is attached to surgical device 16. In one embodiment, connectors 11 electrically connect first section 13 and second section 9 of conductor 17. An electrically insulative material, such as heat shrink, may cover and insulate connectors 11. Although the drawings show three connectors 11, electrosurgical system 10 may include more or fewer connectors 11. The number of connectors 11 may depend on the number of energy transmitting apparatuses of conductor 17.

In addition to conductor 17, bore 4 of tubular structure 14 is configured to receive at least one conduit 15. As seen in FIG. 1, a fluid delivery source 18 supplies cooling fluid to electrosurgical system 10 through conduit 15. Conduit 15 is in fluid communication with fluid delivery source 18 and is configured to carry a cooling fluid towards surgical device 16. The present disclosure contemplates that conduit 15 may be a closed fluid channel. During operation, fluid delivery source 18 supplies cooling fluid to conduit 15, the cooling fluid then flows through conduit 15 towards surgical device 16 and extracts at least part of the heat generated on surgical device 16, and thereafter, the cooling fluid flows away from surgical device 16.

Conduit 15 can include an inflow portion 21 and an outflow portion 23. Inflow portion 21 carries cooling fluid towards surgical device 16 whereas outflow portion 23 carries cooling fluid away from surgical device 16. Inflow portion 21 of conduit 15 is in fluid communication with fluid delivery source 18 and may have a first section 21a and a second section 21b operatively connected to each other. Conduit junction 20 connects the distal end of first section 21a of inflow portion 21 with the proximal end of second section 21b of inflow portion 21. The proximal end of first section 21a is operatively attached to fluid delivery source 18 and the distal end of second section 21b is operatively attached to surgical device 16. In one embodiment, a luer fitting 28 connects first section 21a and second section 21b of inflow portion with one another. Luer fitting 28 can be disposed within a body 22 of conduit junction 20. Although the drawings illustrate luer fitting 28 interconnecting first and second sections 21a, 21b of inflow portion 21, any suitable fitting can be used to operatively couple these two sections 21a, 21b.

Similarly, outflow portion 23 of conduit 15 may have a first section 23a and a second section 23b in fluid communication with each other. The proximal end of first section 23a of outflow portion 23 is attached to fluid delivery source 18 and the distal end of second section 23b of outflow portion 23 is secured to surgical device 16. Conduit junction 20 operatively couples the distal end of first section 23a with the proximal end of second section 23b of outflow portion 23. Luer fitting 28 disposed within the body 22 of conduit junction 20 is shown interconnecting first section 23a and second section 23b of outflow portion 23. One skilled in the art, however, will recognize that any suitable fitting may be used to interconnect first section 23a and second section 23b of outflow portion 23 and that the fitting may be disposed within conduit junction 20.

Figure 4:
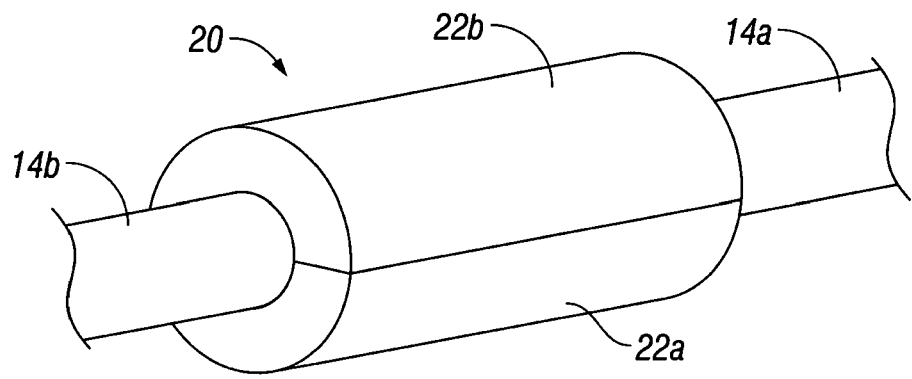
FIG. 4 is a perspective view of the conduit junction of FIG. 3 in a closed position.
Figure 5:
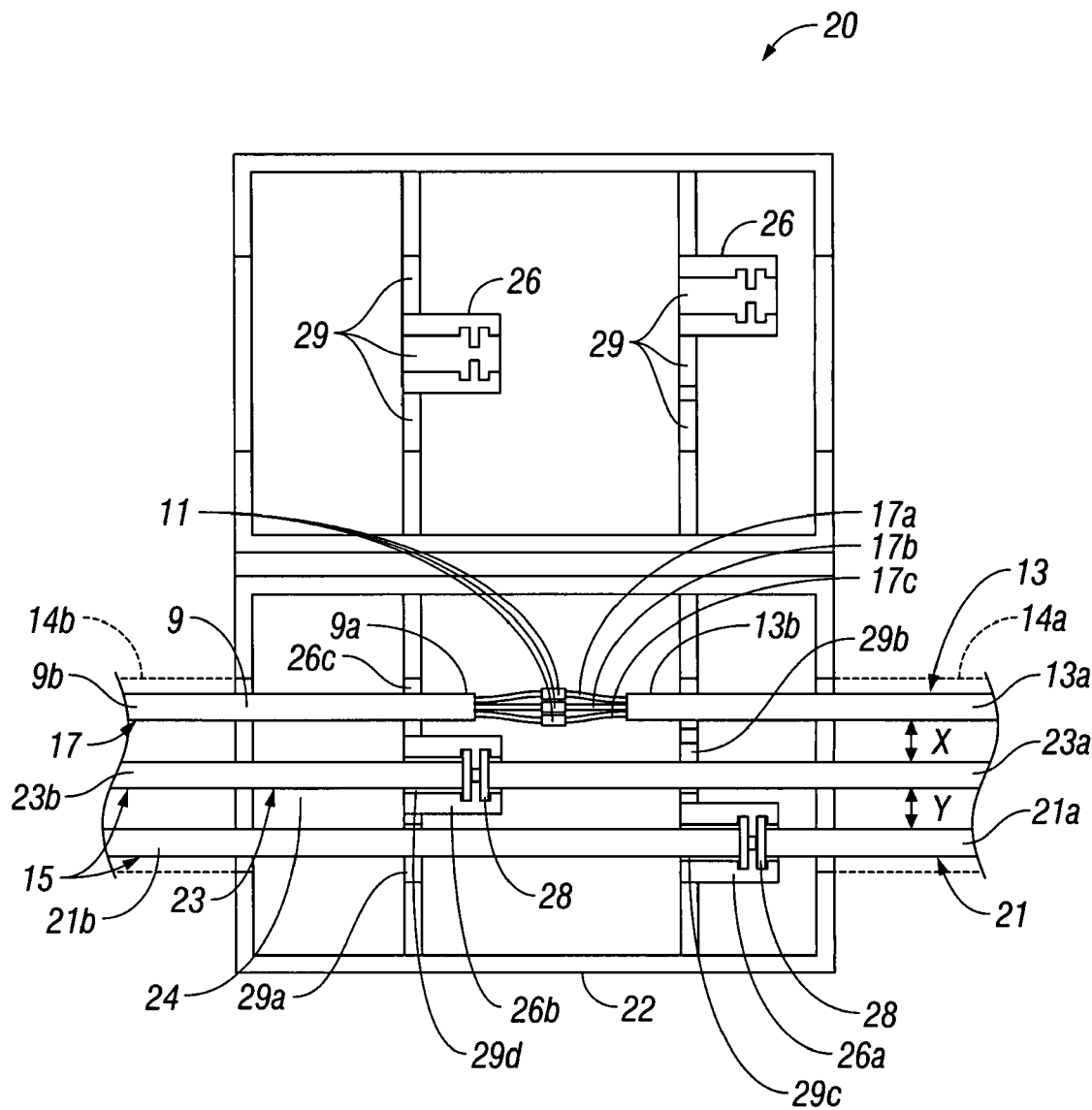
FIG. 5 is a side elevational view of the conduit junction of FIG. 3 in an open position.

The presently disclosed electrosurgical system 10, as previously discussed, includes a conduit junction 20 disposed in mechanical cooperation with tubular structure 14. As seen in FIGS. 3 and 4, conduit junction 20 has a body 22 with a lumen 24 and at least one positioning structure 26. Lumen 24 of body 22 is configured to receive at least a portion of tubular structure 14. In the depicted embodiment, body 22 includes a first section 22a and a second section 22b and has an elongate structure. Body 22, however, can have other suitable structures. First section 22a and second section 22b of body 22 can be pivotably connected to one another and their shapes may be substantially similar. A hinge or any other suitable member may pivotably connect first section 22a and second section 22b of body 22. In addition, first section 22a and second section 22b of body 22 move with respect to each other between a first position and a second position. In the first position, first section 22a and second section 22b allow access to positioning structures 26, as illustrated in FIGS. 3 and 5. On the other hand, when first section 22a and second section 22b of body 22b are placed in the second position, the positioning structures 26 are inaccessible, as shown in FIG. 4.

Body 22 of the conduit junction 20 has at least one positioning structure 26. The embodiment shown in FIGS. 3 and 5 includes three positioning structures 26a, 26b, and 26c. Regardless of the number of positioning structures 26 in body 22, positioning structures 26 are disposed in mechanical cooperation with the lumen 24. Positioning structures 26 are adapted to position at least one of the conductor 17 and the conduit 15 within body 22. In addition to positioning conductor 17 and conduit 15, positioning structures 26 can also secure at least one of conductor 17 and conduit 15 in body 22 of conduit junction 20. Further, positioning structures 26 may be configured to a minimum distance between conduit 15 and conductor 17 to reduce heat transfer therebetween. As shown in FIG. 5, positioning structures 26 can be adapted to maintain a distance X between conductor 17 and outflow portion 23 of conduit 15. Similarly, positioning structure 26 can be designed to maintain a distance Y between the inflow portion 21 and the outflow portion 23 of conduit 15. In one embodiment, distance X is greater than distance Y. An embodiment of the present disclosure includes a conduit junction 20 having two positioning structures 26a, 26b that position and secure inflow portion 21 and outflow portion 23 of conduit 15 within body 22, as shown in FIGS. 3 and 5. An additional positioning structure 26c is shown that positions conductor 17 within body 22. In this embodiment, positioning structures 26a, 26b, 26c maintain a minimum distance between conduit 15 (e.g. inflow portion 21) and conductor 17. Moreover, positioning structures 26a, 26b, 26c can be configured to hold luer fitting 28 or any other suitable fitting to facilitate the connections between first and second sections 21a, 21b of inflow portion 21; first and second sections 23a, 23b of outflow portion 23; and first and second sections 13, 9 of conductor 17.

Positioning structures 26 can further include at least one rib pocket 29. Rib pockets 29 are adapted to hold conduit 15, conductor 17, and/or fitting 28 interconnecting two sections of conduit 15 and/or conductor 17. As illustrated in FIGS. 3 and 4, a first rib pocket 29a can position and secure inflow portion 21 of conduit 15 and another rib pocket 29b may position and secure outflow portion 23 of conduit 15. A separate rib pocket 29c can specifically hold a fitting, such as luer fitting 28, operatively coupling first section 21a and second section 21b of inflow portion 21. In a similar vein, an additional rib pocket 29d can hold a fitting operatively joining first section 23a and second section 23b of outflow portion 23. Alternatively, rib pocket 29 may itself include a fitting interconnecting first section 21a and second section 21b of inflow portion 21 and/or a fitting operatively coupling first section 23a and second section 23b of outflow portion 23.

In operation, conduit junction 20 may be utilized with electrosurgical system 10 or any other suitable surgical system. A method of using conduit junction 20 includes assembling or integrating conduit junction 20 to electrosurgical system 10. To integrate conduit junction 20 and electrosurgical system 10, a user interconnects first section 14a and second section 14b of tubular structure 14. First and second section 14a, 14b of tubular structure 14 can be interconnected by coupling sections of the inflow and outflow portions 21, 23 of conduit 15 as well as a section of conductor 17.

An operator can connect first section 21a and second section 21b of inflow portion 21 of conduit 15 with a fitting (e.g. luer fitting 28). First section 23a and second section 23b of outflow portion 23 of conduit 15 can also be coupled with a fitting. These fitting may then be placed in rib pockets 29 of positioning structures 26. A user can also couple first section 13 and second section 15 of conductor 17 with at least one electrical connector 11. Thereafter, electrical connector 11 can be positioned in rib pocket 29 of positioning structure 26. After placing the fittings and connectors 11 in rib pockets 29, the user may move conduit junction 20 to its second position, as seen in FIG. 4, by moving the second section 22b of body 22 in the direction indicated by arrow "A" in FIG. 3.

Although the present disclosure describes specific embodiments, these embodiments should not be construed as limitations on the present disclosure, but merely exemplifications of the embodiments of the present disclosure. Those skilled in the art will envision many other variations that are within the scope and spirit of the present disclosure as defined by the claims appended hereto.

What it is claimed is:

1. A conduit junction for use with a surgical system, comprising:
    a body having a lumen defined therein, the lumen being configured to receive at least a portion of a tubular structure, wherein the tubular structure includes at least one of a conductor and a conduit; and
    at least one positioning structure disposed in mechanical cooperation with the lumen, the at least one positioning structure being adapted to position at least one of the conductor and conduit with the body, wherein the at least one positioning structure includes at least one luer fitting.

2. The conduit junction of claim 1, wherein the body includes a first section and a second section.

3. The conduit junction of claim 2, wherein the first section of the body and the second section of the body are pivotably connected with each other.

4. The conduit junction of claim 2, wherein the first section of the body and the second section of the body are movable with respect to each other between a first position where the at least one positioning structure is accessible and a second position where the at least one positioning structure is inaccessible.

5. The conduit junction of claim 1, wherein the at least one positioning structure is configured to secure at least one of the conductor and the conduit at least partially within the body.

6. The conduit junction of claim 1, wherein the at least one positioning structure includes at least one rib pocket.

7. The conduit junction of claim 1, wherein the at least one positioning structure is configured to maintain a minimum distance between the conductor and the conduit.

* * * * *